United States Patent [19]
Minkus et al.

[11] Patent Number: 5,460,617
[45] Date of Patent: Oct. 24, 1995

[54] SYRINGE PLUNGER WITH INTERMEDIATE PUSHING SURFACE

[75] Inventors: Marc S. Minkus, Highland Park; John S. Ziegler, Arlington Heights, both of Ill.

[73] Assignee: Abbott Laboratories, Abbott Park, Ill.

[21] Appl. No.: 282,138

[22] Filed: Jul. 28, 1994

[51] Int. Cl.$^6$ ................................................. A61M 5/315
[52] U.S. Cl. ........................................... 604/218; 604/227
[58] Field of Search ........................... 604/218, 227, 604/228

[56] References Cited

U.S. PATENT DOCUMENTS

| | | | |
|---|---|---|---|
| 2,532,598 | 12/1950 | Boeger | 604/227 X |
| 3,316,909 | 5/1967 | Cowley | 604/227 |
| 3,388,941 | 6/1968 | Marcus | 604/227 |
| 3,640,278 | 2/1972 | Friedman | 604/227 X |
| 4,060,083 | 11/1977 | Hanson | 604/227 |
| 4,340,051 | 7/1982 | Leibinsohn | 604/227 |
| 5,226,897 | 7/1993 | Nevens et al. | 604/218 |

*Primary Examiner*—John D. Yasko
*Assistant Examiner*—Adam J. Cermak
*Attorney, Agent, or Firm*—A. Nicholas Trausch

[57] ABSTRACT

The present invention is directed to a syringe plunger for use to administer a solution front a syringe of the type having an axially slidable piston sealing an axially extending barrel having a nozzle. The plunger includes a rigid stem member axially extending from a distal end to a proximal end. The plunger also includes threads or other attaching mechanism at the proximal end of the stem for removable attachment to the slidable piston. The stem member includes a first surface at the distal end of the stem for application of axial force to the stem so as to move the slidable piston in the barrel. Advantageously according to the invention, the stem also includes a second surface at an axially intermediate position on the stem for alternative application of axial force to the stem so as to initially move the slidable piston in the barrel, which is especially convenient for syringe users with small hands.

7 Claims, 1 Drawing Sheet

5,460,617

SYRINGE PLUNGER WITH INTERMEDIATE PUSHING SURFACE

FIELD OF THE INVENTION

The present invention relates generally to syringes, and more particularly, to a plunger component with an intermediate pushing surface which allows a user with small hands to administer the contents of a syringe without stretching his or her hands uncomfortably.

BACKGROUND OF THE INVENTION

Syringes typically include a plunger which is a rigid stem used to move a slidable piston axially through a solution-filled barrel to push solution through a nozzle at the end of the barrel.

In order to ensure that all the solution in the barrel is administered through the syringe nozzle, the plunger stem must be at least as long as the syringe barrel. For small volume syringes, 5 cc and 10 cc syringes, for example, the syringe barrel may be approximately three to four inches (3–4") long. Thus, the small volume syringe plunger stem is often in the range of approximately three to four inches long. Usually a user, even with small hands, can grasp the syringe barrel at the flange tabs between two fingers and extend the thumb to the distal end of the extending plunger stem. Then, when the user applies force on the plunger pushing surface, the piston moves through the barrel and solution is administered through the end nozzle.

However, for larger syringes, for example, 50 cc or 60 cc syringes, the barrel is typically longer than four inches (4") and often longer than five inches (5"). Consequently the plunger is also longer than approximately four inches. A user with small hands will have great difficulty in using these large syringes with only one hand. For example, a person with small hands will have great difficulty in positioning the wide diameter syringe barrel between two fingers and firmly hold the barrel while extending the thumb rearward four inches or more to the plunger pushing surface. Even if the user accomplishes this stretch of the hand, the small handed user may have difficulty generating enough axial force to push the plunger into the barrel to begin administration of the solution.

Often a small handed riser using a large volume syringe must resort to two handed operation of the syringe. In many situations, two handed use limits the user's ability to perform other tasks. These other tasks include opening or closing flow control devices, or other manipulation that are normally most efficiently performed concurrent with the fluid administration. Thus, it is a disadvantage to have a large volume syringe that cannot be used by all users in the same one-handed manner that is used for small volume syringes.

It is therefore desirable to provide a syringe plunger for large volume syringes that would accommodate one-handed administration by small handed people. Such a syringe plunger would enable a small handed person to perform the procedures in an expected manner.

The present invention provides a syringe plunger with an intermediate pushing surface positioned on the stem between the proximal end of the stem and the distal pushing surface of the stem that will accommodate one-handed administration of most syringes by small handed persons.

SUMMARY OF THE INVENTION

The invention provides a syringe plunger for a syringe of the type having an axially slidable piston in an axially extending barrel wherein the plunger includes an axially extending rigid stem member having piston attachment structure such as threads at a proximal end. At the distal end of the plunger stem member is a first pushing surface for application of axial force by the user so as to move the piston through the barrel. A second pushing surface is provided at an axially intermediate position on the plunger stem for the alternative application of axial force to the stem by a user, for example, with small hands, so as to initially move the slidable piston in the barrel.

The plunger stem member is configured so as to allow the slidable piston to be axially movable within the barrel without causing interfering or binding contact of the stem with the barrel which would thus prevent axial movement of the piston.

In a preferred embodiment of the syringe plunger, the first and second or intermediate pushing surfaces are substantially perpendicular to the axis of the stem. Furthermore, the intermediate surface is positioned at approximately the axial midpoint of the stem.

The preferred embodiment of the syringe plunger also includes an axial clearance space along at least one edge portion of the intermediate pushing surface. The clearance space extends axially through a radially central portion of the stem to form a cutout, for example, so as to allow the thumb of the user to comfortably and fully contact the second pushing surface.

In a further embodiment of the syringe plunger, a predetermined position on the plunger, such as the intermediate pushing surface can be used to indicate that a preselected amount of solution has been administered from the syringe. For example, when the axial position of the intermediate pushing surface is axially coincident with a fixed position on the syringe barrel, the coincident positions can be precalibrated to indicate that a preselected amount of solution has been administered.

Accordingly, when a small handed user initially administers a first portion of the solution from a large volume syringe, the plunger stem is pushed from the intermediate position by the thumb in a comfortable manner without stretching the hand. When the intermediate pushing surface has been moved to coincide with the fixed indicating position on the syringe barrel, the solution administration can be temporarily stopped. Then the thumb can be repositioned on the end pushing surface and the solution administration can be completed.

Numerous other advantages and features of the present invention will become readily apparent from the following description of the invention, the claims, and the accompanying drawings.

DESCRIPTION OF THE PREFERRED EMBODIMENTS

While this invention is susceptible of embodiments in many different forms, the specification and accompanying drawing discloses only one specific form as an example of this invention. The invention is not intended to be limited to the embodiment described, the scope of the individual invention being pointed out in the appended claims.

Figure 1:
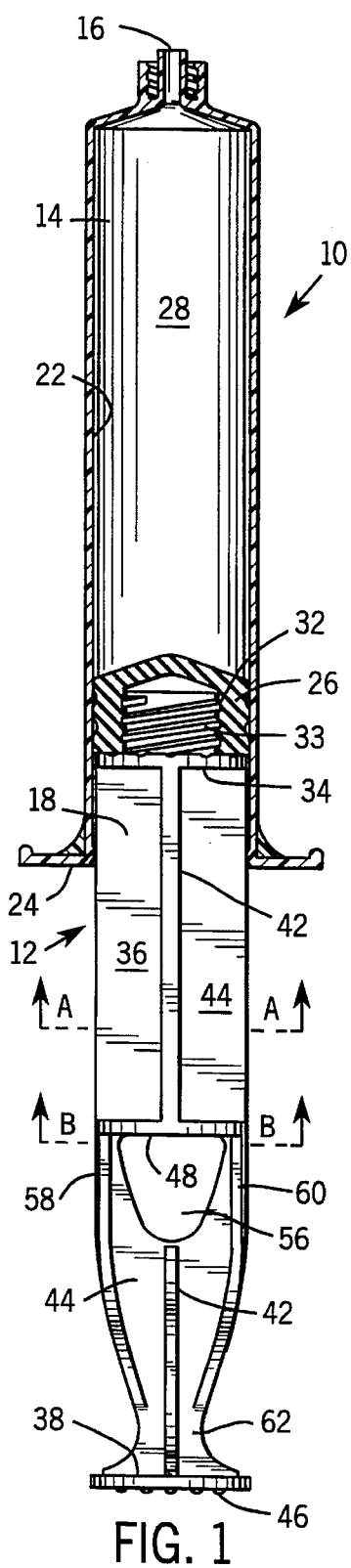
FIG. 1 is a sectional view of a syringe including a solution-filled syringe barrel and an attached syringe plunger according to the present invention.
Figure 2:
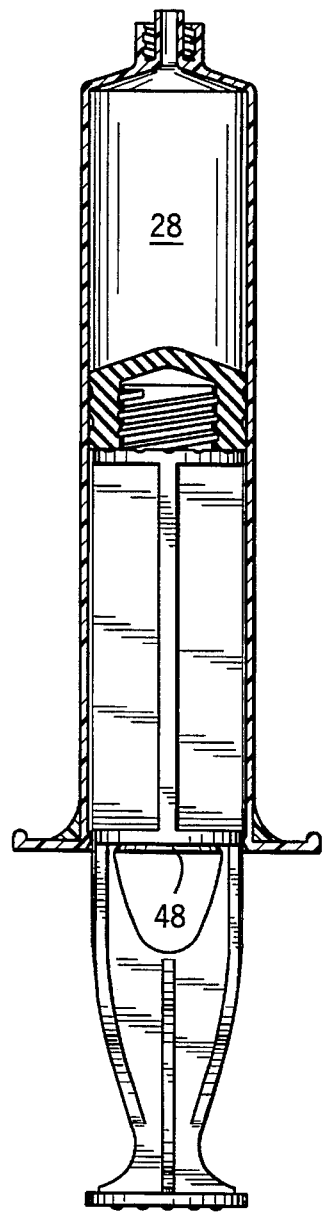
FIG. 2 is a cross-sectional view of the syringe according to the present invention showing a partial administration of the solution.
Figure 3:
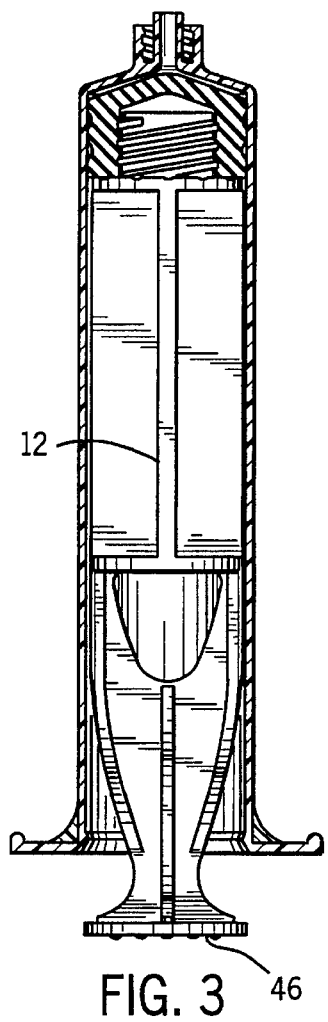
FIG. 3 is a cross-sectional view of the syringe plunger according to the present invention showing a complete administration of the solution.

Referring now to FIGS. 1–3, a syringe assembly 10 includes a syringe plunger 12 according to the present invention and a barrel 14 of conventional construction.

As such, the barrel 14 is preferably an axially extending cylinder having an administration nozzle 16 at a proximal end and an open distal end, generally indicated at 18. The barrel is preferably molded of a suitable plastic material or formed of glass so as to be compatible with the solutions to be administered. The barrel also includes a smooth, interior sidewall 22 which extends the whole length of the barrel. Radially extending barrel flange tabs 24 may be provided at or near the distal end of the barrel.

A sealingly slidable piston 26 is fitted in the distal end of the syringe barrel. The piston is preferably molded of an elastomeric material. The piston is constructed and arranged for sealing and sliding contact with the interior sidewall 22 of the syringe barrel. A removable nozzle cap (not shown) seals the nozzle 16. Thus, a sealed solution chamber 28 is formed in the open-ended barrel 14 by the nozzle 16 and nozzle cap, the interior sidewall 22 of the barrel, and the sealingly slidable piston 26.

To administer the solution through the nozzle 16, the elastomeric piston 26 is moved from the distal end of the barrel to the proximal end of the barrel, forcing the solution through the nozzle. The rigid, axially extending plunger stem member 12, is utilized to push the piston to the proximal end of the syringe barrel. In a preferred embodiment of the plunger, structure such as threads 32 at the proximal end of the plunger stem are provided for removable attachment to the piston 26, such as, by mating threads 33 in the distal face of the piston. Other attachment structure includes, for example, a radial flange on the proximal end of the stem that can mate with an undercut in the piston. An embodiment of this type, however, results in a plunger-piston connection that is less detachable than the threaded type.

The attaching construction is positioned at a radial flange 34 on the proximal end of the plunger stem. The stem 36 is a rigid, axially-extending construction whose length is usually greater than the length of the syringe barrel 14. The stem ends in a second radial flange 38 at the distal end of the stem. In the preferred embodiment of the plunger, the stem is constructed of two axially-extending rib members 42 and 44. The rib members 42 and 44 perpendicularly intersect along the axis of the stem to provide for the structural rigidity of the stem. This conventional intersecting rib construction reduces the amount of material and cost necessary to produce an acceptable rigid structure. The intersecting rib construction can be best seen in the cross-section of FIG. 1a. Other rigid stem construction such as a hollow cylinder is also considered to be with the scope of the invention.

An end pushing surface 46 is located at the distal end of the stem. An intermediate pushing surface 48 is conveniently located on the plunger at approximately the midpoint between the proximal end and the distal end of the plunger. The pushing surfaces 46 and 48 are substantially perpendicular to the axis of the plunger stem.

Figure 1A:
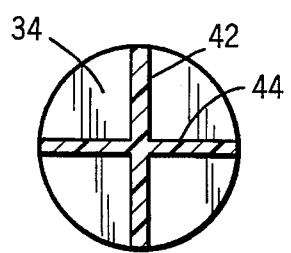
FIG. 1a is a cross-sectional view of the syringe plunger at section line a—a.
Figure 1B:
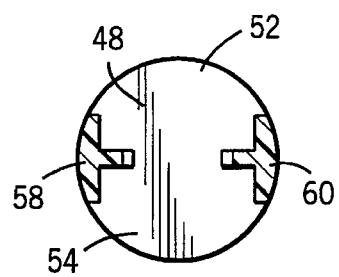
FIG. 1b is a cross-sectional view of the cutout space of the syringe plunger according to the present plunger at section line b—b.

As seen in FIG. 1b, the intermediate push surface 48 has an axially cleared space along at least one edge portion of the perpendicular surface as shown generally by 52 and/or 54. Notably, structural rib 42 as seen in FIG. 1 and FIG. 1a, is axially interrupted as shown in FIG. 1b, so as to produce a radially flat intermediate surface 48 which is perpendicular to the axis of the stem 36. The flat surface is large enough to accommodate the thumb of the syringe user. As seen with reference to FIG. 1, the flat surface of the axial clearance space 52/54 also extends through a radially central portion of the stem as shown by the cutout 56. Thus, the central portion of rib 44 is also interrupted on the distal side of the intermediate push surface 48.

To structurally compensate for the complete removal of structural rib 42 and the substantial removal of the center portion of rib 44 at the cutout space 56, side ribs 58 and 60 are added substantially parallel to and overlapping the removed portion of rib 42. The side ribs 58 and 60 compensate for the loss of rib structure material at the center portions of the stem.

The distal end of the plunger stem 12 is also provided with a waist portion 62 which allows the plunger stem to be pulled back if it is desired that the syringe also perform aspiration as well as administration of solution.

In operation, a syringe which includes the syringe plunger 12 of the present invention is advantageously used as follows. A syringe barrel 14 and the syringe plunger 12 of the present invention are assembled together and filled as shown in FIG. 1. To administer the solution in the syringe, a user typically holds the syringe barrel 14 between two fingers at the barrel flange tabs 24. The user then extends his or her thumb to apply axial force to the end pushing surface 46 on the syringe plunger. If the syringe is small enough in size and/or the user's hands are large enough, the user can comfortably push on the end pushing surface 46.

However, for large syringes having long barrel and plunger stem lengths and/or for users having small hands, the user may be more comfortable initially applying axial force with his or her thumb at the intermediate pushing surface 48. The user can continue pushing at 48 until the intermediate surface is axially coincident with the end of the barrel such as at the flange tabs 24 as shown in FIG. 2.

The coincidence of the intermediate push surface and the flange tabs can be readily used as a convenient indicator that a predetermined amount of solution or pre-selected fraction of a dose has been administered from the syringe. For example, with the proper structural dimensioning of the axial position of the intermediate surface 48 on the stem, the concurrence of the intermediate surface 48 and the flange tabs 24 can indicate that one half of the solution in the syringe has been administered. Different and multiple pre-selected indicating structures on the plunger stem 36 can be provided to indicate various portions of the full solution dose, such as one quarter, one half and/or three quarters dose, have been administered.

At the half-way point in the administration of the solution, for example, the user can now comfortably reposition his or her thumb on the distal pushing surface 46 and continue the administration of the fluid through the nozzle as shown in

FIG. 3.

The syringe plunger of the present invention can be used with any syringe or other axially movable device that is movable by an axially-applied force. The intermediate push position plunger 12 of the present invention was primarily developed for use with large volume syringes of the 50 or 60 cc volume type, specifically, medical solution syringes. For these type of syringes, a standard syringe barrel 14 may be in excess of four to five inches (4–5") which requires that the syringe plunger be on the order of greater than four to five inches. A person with small hands may find it uncomfortable and be unable to apply the required axial force with one hand when the syringe barrel 14 is held between two fingers and the thumb is extended to push on the end pushing surface 46 of such a long plunger stem.

Thus, it is believed that the addition of the intermediate pushing surface 48 of the present invention to the plunger 12 allows a small handed person to comfortably and with reasonable effort administer solutions front large volume syringes. The intermediate pushing surface is preferably located at approximately the midpoint of the plunger stem and thus is only two to three inches (2–3") from the flange tabs and/or the end of the barrel. The axial cutout 56 at the intermediate surface is approximately one half to one inch (½–1") in height. Thus, a small handed user can comfortably use a larger volume syringe in a manner similar to the conventional one handed manner used with small volume syringes. This, for example, can be important in medical situations since medical protocols and procedures for the administration of solutions via syringes are often established which require one hand for the push administration while the other hand is free to manipulate other associated medical devices, such as fluid flow controllers, or to attend to the patient, for example.

The intermediate pushing surface and/or dose indicating means of the present invention involves no extra material, parts or manufacturing effort and is therefore essentially cost free. Either or both can be used instantly without any pre-adjustment. Either or both can be ignored if not needed with no penalty in convenience or cost.

It will be readily apparent from the foregoing detailed description of the invention and from the illustrations thereof that numerous variations and modifications may be affected without the departing from the true spirit and scope of the novel concepts and principals of this invention.

What is claimed is:

1. A syringe plunger for use to administer a solution from a syringe of the type having an axially slidable piston sealing an axially extending barrel, the plunger comprising:

a rigid stem member axially extending from a distal end to a proximal end;

means at the proximal end of the stem for attachment to a piston slidable in a barrel;

a first surface at the distal end of the stem for application of axial force to the stem so as to move the slidable piston axially in the barrel wherein the first surface is substantially perpendicular to the axis of the stem;

means at an axially intermediate position on the stem for alternative application of axial force to the stem so as to initially move the slidable piston axially in the barrel wherein the intermediate means is a second surface that is substantially perpendicular to the axis of the stem and is approximately at the axial midpoint between the proximal and distal end of the stem and includes an axial clearance space extending along at least one edge portion of the second surface and extending through a radially central portion of the stem on the distal side of the second surface; and the stem member having a radial configuration so as to allow the slidable piston to be axially movable in the barrel without the radial configuration of the stem causing contact of the stem with the barrel to limit the axial movement of the slidable piston.

2. The syringe plunger of claim 1 wherein the attachment means is removable from the slidable piston.

3. The syringe plunger of claim 1 wherein the attachment means is a threaded attachment.

4. The syringe plunger of claim 1 wherein the axial midpoint is in the range of 2 to 3 inches from the proximal end of the stem and the axial clearance space extends in the range of 0.5 to 1 inch from the second surface.

5. The syringe plunger of claim 1 further including means on the stem for indicating that at least one preselected amount of solution has been administered from the barrel of the syringe as the plunger is moved.

6. The syringe plunger of claim 5 wherein the indicating means includes at least the intermediate axial position of the second surface of the stem which indicates at least one preselected amount of solution has been administered as indicated relative to at least one fixed position on the barrel.

7. The syringe plunger of claim 6 wherein at least one fixed position on the barrel is the distal end of the barrel.

* * * * *